United States Patent [19]

Stewart

[11] Patent Number: 5,156,911

[45] Date of Patent: Oct. 20, 1992

[54] SKIN-ACTIVATED TEMPERATURE-SENSITIVE ADHESIVE ASSEMBLIES

[75] Inventor: Ray F. Stewart, Redwood City, Calif.

[73] Assignee: Landec Labs Inc., Menlo Park, Calif.

[21] Appl. No.: 350,723

[22] Filed: May 11, 1989

[51] Int. Cl.$^5$ ................................................. B32B 7/12
[52] U.S. Cl. ..................................... 428/355; 424/448; 424/449
[58] Field of Search ............... 428/444, 455, 355, 343; 424/448, 449

[56] References Cited

U.S. PATENT DOCUMENTS

| | | | |
|---|---|---|---|
| 3,284,423 | 11/1966 | Knapp | 526/218.1 |
| 3,299,010 | 1/1967 | Samour | 428/355 |
| 3,535,295 | 10/1970 | Davis et al. | 525/193 |
| 3,612,053 | 10/1971 | Pratt | 604/338 |
| 3,635,754 | 1/1972 | Beede | 428/349 |
| 3,690,937 | 9/1972 | Guse et al. | 427/208.4 |
| 3,838,079 | 9/1974 | Kosaka et al. | 524/271 |
| 4,199,646 | 4/1980 | Hori et al. | 428/344 |
| 4,323,557 | 4/1982 | Rosso et al. | 424/448 |
| 4,404,243 | 9/1983 | Terpay | 428/354 |
| 4,551,388 | 11/1985 | Schladerman | 428/355 |
| 4,675,009 | 6/1987 | Hyma et al. | 424/449 |
| 4,789,285 | 9/1988 | Pesmusser | 423/355 |
| 4,880,683 | 11/1989 | Stow | 428/355 |
| 4,925,908 | 5/1990 | Bernard et al. | 526/320 |

OTHER PUBLICATIONS

Flanagan, *Handbook of Adhesive Bonding* (McGraw-Hill Book Co., 1973) ch. 8, pp. 1-17.
Landrock, *Adhesives Technology Handbook* (Noyes Publications, 1985) pp. 154-156.
Miyauchi, *J. Polymer Sci.: Polymer Chem. Edition* 19:1871-1873 (1981).
Satas, *Handbook of Pressure Sensitive Adhesives Technology* (Van Nostrand Reinhold Co. Inc., 1982) ch. 4, pp. 50-77, ch. 13, pp. 299-330, ch. 14, pp. 331-425, ch. 29, pp. 575-585.
Temin, Encyclopedia of Polymer Science and Engineering vol. 13 (John Wiley & Son's, 1988) pp. 345-368.

*Primary Examiner*—Thurman K. Page
*Assistant Examiner*—Leon R. Horne
*Attorney, Agent, or Firm*—Morrison & Foerster

[57] ABSTRACT

An adhesive assembly is provided having a temperature-sensitive adhesive composition coated on the surface of a selected substrate. The adhesive composition is nontacky or slightly tacky at room temperature, but is aggressively tacky at skin temperature. The assemblies include adhesive tapes, bandages, films and the like.

20 Claims, No Drawings

SKIN-ACTIVATED TEMPERATURE-SENSITIVE ADHESIVE ASSEMBLIES

TECHNICAL FIELD

The present invention relates to temperature-sensitive adhesive compositions, and more particularly concerns skin-activated temperature-sensitive adhesive assemblies, e.g., adhesive tapes and the like.

BACKGROUND

Pressure-sensitive adhesives (PSA) are well known and are used for a variety of industrial, consumer and medical applications. Pressure-sensitive adhesives are characterized as being normally tacky and exhibiting instant tack when applied to a substrate. A variety of polymers have been used to manufacture PSA, for example, acrylic and methacrylic ester homo- or copolymers, butyl rubber-based systems, silicones, urethanes, vinyl esters and amides, olefin copolymer materials, natural or synthetic rubbers, and the like.

Typically, the bond strength of a PSA remains the same or increases with time after application to a substrate. Increased bond strength may result from increased polymer flow or improved wetting over a period of time, or it may result from hydrogen bonding to a polar substrate or from covalent or ionic chemical interactions. Removal of an adhesive after application to a substrate is often desirable. For example, tape may be applied to a substrate to mask off a portion during a painting operation, at the completion of which the tape must be removed. Wallpaper can be applied with a PSA and removal at a future date is usually desirable. Adhesives applied to human skin, for example on a bandaid, wound dressing, transdermal drug delivery device, or monitoring or stimulating electrode, must be removed at a later date. In all of these instances and many others, it is desirable to be able to readily remove the adhesive without the need for harsh chemicals or special equipment.

The ideal performance characteristics of an adhesive intended for use on human skin, specifically, present difficult and conflicting technical requirements. The ideal medical adhesive should, first of all, be nonirritating yet bond quickly to skin at the intended site of use. At the same time, clearly, it should not stick to other objects until it is actually applied to the target site. The adhesive should maintain its bond for as long a period of time as necessary and be resistant to inadvertent removal. Furthermore, the adhesive should not be weakened or destroyed by exposure to moisture or high humidity. Finally, in order to provide protection to a wound or to maintain the integrity of placement of an electrode or other device the adhesive should resist skin movement and be able to transfer a mechanical load from the adhesive backing to the skin.

The present invention is directed to adhesive assemblies formulated with such an adhesive composition. The composition is substantially non-tacky at room temperature and tacky at skin temperature. In one embodiment, adhesion is "temperature reversible". That is, adhesive articles may be formulated so as to stick aggressively to the skin but can nevertheless be readily removed therefrom with near-zero peel strength by simple chilling.

DESCRIPTION OF THE PRIOR ART

S.C. Temin, in the *Encyclopedia of Polymer Science and Engineering*, vol. 13 (New York: John Wiley & Sons, 1988), at pp. 345–368, and the *Handbook of Pressure-Sensitive Adhesive Technology*, ed. Donates Satas (New York: Van Nostrand Reinhold Co., Inc., 1982), both provide a comprehensive overview of medical and other adhesives. A. H. Landrock, *Adhesives Technology Handbook* (Park Ridge, N.J.: Noyes Publications, 1985), pp. 154–156, and T. Flanagan, "Hot-melt Adhesives", in the *Handbook of Adhesive Bondinc*, ed. C.V. Cagle (New York: McGraw-Hill, 1982), at pp. 8-1 to 8-17, describe hot-melt adhesives, i.e., adhesives which are applied to a substrate as a melt and which solidify and bond upon cooling. In contrast to the adhesive compositions of the present invention, hot-melt adhesives involve flowable polymers and do not allow for reversible adhesion.

U.S. Pat. No. 3,635,754 to Beede describes a temporary pressure-sensitive adhesive product which must be activated by heating. That is, prior to use, the product must be heated in order to render the adhesive tacky. After cooling, the product remains tacky for an extended period of time. By contrast, applicant's adhesive product requires no heat activation, and, in the embodiment wherein adhesion is temperature-reversible, tack is very quickly lost upon cooling.

U.S. Pat. No. 3,284,423 to Knapp describes a pressure-sensitive, cross-linked adhesive copolymer which is claimed to be storage stable in solution but readily cured when coated and heated. The copolymer consists of acrylic acid esters, lower alkyl acrylates, acrylic acid and glycidyl acrylate or methacrylate.

U.S. Pat. No. 3,535,195 to Davis et al. describes a pressure-sensitive, amine-containing adhesive which is stated to exhibit good tack yet be easily removable from a substrate.

U.S. Pat. No. 3,690,937 to Guse et al. relates to pressure-sensitive adhesives formulated from di-alkyl fumarates.

U.S. Pat. No. 3,838,079 to Kosaka et al. describes copolymer resins prepared from alkyl acrylates (1-20C) and maleic anhydride.

U.S. Pat. No. 3,299,010 to Samour describes a variety of adhesive compositions, some of which contain C-12 to C-24 residues. The patent teaches that the higher alkyl residues must be branched in order to avoid crystallinity. Some of the compositions contain acrylamido or other polar groups, and claims of adhesion to moist skin are made.

U.K. Patent No. 870,022, inventors Dahlquist and Zenk, teaches the use of a copolymer of octadecyl acrylate, acrylonitrile, ethyl acrylate, and acrylic acid as a low adhesion backsize on a pressure-sensitive adhesive tape.

PCT Publication No. WO84/03837 teaches the use of copolymers which contain a polyalkylene oxide monomer in addition to acrylate. The polyoxyalkylene moiety is stated to impart hydrophilic behavior to the adhesive composition, thus facilitating adhesion to moist skin.

European Patent Application Publication No. 062682 describes the use of a copolymer of dodecyl methacrylate as an adhesive carrier for nitroglycerine. Small amounts of other monomers are added to improve properties, e.g., acrylic acid and short chain acrylates.

The following references relate to side-chain crystallizable polymers: *J. Polymer Sci.: Macromolecular Re-* view 8:117 (1974) and *J. Polymer Sci.: Polymer Chemistry Edition* 19:1871–1873 (1981).

SUMMARY OF THE INVENTION

It is thus a primary object of the present invention to provide a temperature-sensitive adhesive assembly for application to the skin.

It is also an object of the invention to provide a medical adhesive assembly, specifically, which can be removed from the skin with less pressure, pulling and trauma than conventional adhesive tapes and bodies necessitate.

It is another object of the invention to provide a temperature-sensitive, pre-positionable medical adhesive assembly which is substantially nontacky at room temperature, becomes tacky upon application to skin, and retains tack indefinitely.

It is still another object of the invention to provide a medical adhesive assembly which is aggressively tacky at skin temperature, and which rapidly loses tack upon cooling.

It is a further object of the invention to combine the advantages and characteristics of the latter two embodiments, in providing a pre-positionable medical adhesive assembly which is substantially nontacky at room temperature, becomes aggressively tacky upon application to the skin, and rapidly loses tack upon cooling.

It is still a further object of the invention to provide methods of making and using the aforementioned adhesive assemblies.

Additional objects, advantages and novel features of the invention will be set forth in part in the description which follows, and in part will become apparent to those skilled in the art on examination of the following, or may be learned by practice of the invention. The objects and advantages of the invention may be realized and attained by means of the instrumentalities and combinations particularly pointed out in the appended claims.

In one aspect, the invention is directed to a temperature-sensitive, pre-positionable medical adhesive assembly comprising a body member having a surface coated with an adhesive composition that is substantially nontacky at room temperature and tacky at skin temperature. By "pre-positionable" is meant an assembly which can be positioned and maneuvered about, at room temperature, without unwanted adhesion.

In another aspect, the invention is directed to a medical adhesive assembly comprising a body member having a surface coated with an adhesive composition which, while tacky at skin temperature, quickly loses tack upon cooling.

In still another aspect, a medical adhesive assembly is provided which is pre-positionable (i.e., substantially nontacky at room temperature), aggressively tacky at skin temperature, and capable of rapidly losing tack upon cooling.

These adhesive assemblies may be adhesive tapes in which a flexible backing is coated with a selected polymer, or they may comprise casts, splints or other immobilization devices which have been similarly coated. Where the composition provides temperature-reversible adhesion, strong bonding will be provided during use, i.e., between the immobilization device and the skin, but after use, upon cooling, the adhesive becomes substantially nontacky, allowing easy removal of the immobilization device.

DETAILED DESCRIPTION OF THE INVENTION

The invention is thus directed to temperature-sensitive adhesive assemblies useful in a variety of medical applications. The adhesive assemblies comprise body members having a surface which is coated with a temperature-sensitive adhesive composition. The body member may be, for example, an EKG or other type of electrode, a flexible backing in the case of adhesive tape, a surgical dressing, bandaid, medicated bandaid (i.e., a transdermal drug delivery patch) or the like, or it may be a cast, splint, or similar immobilization device. Other skin contact and nonmedical applications are intended to be encompassed by the present invention as well, as the focal point of the invention is not on particular uses of the adhesive assemblies described and claimed herein but on the incorporation of a temperature-sensitive adhesive composition into different types of adhesive assemblies.

Three embodiments are intended to be encompassed by the subject invention: (I) A pre-positionable adhesive assembly which is initially substantially nontacky, i.e., at or below room temperature, but which becomes tacky relatively quickly upon application to skin; (II) an adhesive assembly which may or may not be tacky to start with, but which is aggressively tacky at skin temperature and capable of quickly losing tack upon cooling; and (III) an adhesive assembly in which the characteristics of Embodiments (I) and (II) are combined, i.e., a temperature-reversible system which is initially substantially nontacky, becomes aggressively tacky upon application to skin, and quickly becomes substantially nontacky upon cooling.

In Embodiment (I), the adhesive composition comprises a polymer which has a first-order transition temperature or melting point above room temperature (i.e., approximately 25° C. in most cases) but below skin temperature. Preferably, the first-order transition temperature or melting point will be in the range of about 20° C. to 35° C., more preferably in the range of about 25° C. to 30° C. It is preferred that melting occur rapidly, i.e., over a relatively narrow temperature range, less than about 10° C., preferably less than about 5° C. In Embodiment (I), the adhesive assembly is substantially nontacky up until the moment of application, and becomes tacky upon contact with skin; no external activation of any sort is required. (Melting of most polymers generally takes place over a 5°–10° C. range, and onset of tack occurs at the onset of melting; the melting "point" of the polymers as described herein is actually the temperature at which melting begins).

In this embodiment, the adhesive is typically completely nontacky at room temperature, so that a bandage, wound dressing, or the like formulated with the adhesive composition can be applied, positioned and maneuvered about, if necessary, without unwanted adhesion. In some cases, however, it will be preferred that the adhesive be slightly tacky at room temperature, so that a release liner may adhere to and protect the adhesive coating prior to use. Slight tack at room temperature may be achieved by impregnation of the adhesive composition with standard pressure-sensitive adhesives or incorporation of slightly tacky monomers into the selected polymer.

In Embodiment (II), the adhesive composition comprises a polymer which provides for rapid loss of tack upon simple chilling, e.g., by application of ice, a cold pack, or the like. In this embodiment, the polymer should have a freezing (or "crystallization") point lower than skin temperature, preferably in the range of about 10° C. to 28° C., more preferably in the range of about 15° C. to 25° C. It is also preferable that the polymer crystallize rapidly. To this end, monomers can be incorporated into the polymer which provide for rapid crystallization kinetics. In this embodiment, removal of the adhesive assembly from the skin is greatly facilitated; after use, adhesive tapes, bodies and the like may be readily removed by simple chilling, only slightly below their use temperature, without stretching or pulling on the skin.

In Embodiment (III), the characteristics of the adhesive assemblies of Embodiments (I) and (II) are combined. That is to say, adhesive assemblies in this class display temperature-reversible adhesion; they are substantially nontacky initially, prior to use (at room temperature), they become tacky upon application to skin, and they rapidly lose tack and may thus be removed from skin by cooling. In this embodiment, it is preferred that the polymer of the adhesive assembly have a melting point or first-order transition temperature within the range set forth for Embodiment (I), and a freezing or crystallization temperature within the range set forth for Embodiment (II).

The term "tack" as used hereinabove is intended to designate the tacky or sticky nature of the adhesive composition. Tack can generally be determined by what is referred to as the thumb test in which the thumb is pressed against the surface being considered and then removed to determine the tacky or sticky nature of the surface. A substantially more accurate and reproducible test, however, and the one to which the tack values used in the present specification and claims refer is that designated D 2979 by the American Society for Testing and Materials. In this test values are given in grams of force required to remove the end of a stainless steel rod, 5.0 mm in diameter, from the surface of an adhesive coating at a speed of 10 mm per second to which it has been adhered for 1.0 second (contact speed 10 mm/second). By the terms "substantially nontacky", "slightly tacky" and "tacky", then, is intended, respectively: (1) a tack of less than about 5 g/cm² of force; (2) a tack in the range of 5 g/cm² to about 10 g/cm² of force; and (3) a tack of at least about 10 g/cm² of force.

The polymer in each of Embodiments (I), (II) and (III) is a crystallizable polymer or a functional equivalent of a crystallizable polymer. By polymers which are "functionally equivalent" to crystallizable polymers for purposes of the present invention, applicant intends to include polymers which exhibit the temperature-dependent adhesion properties described above. Crystallizable polymers which may be used in the adhesive composition include both side-chain crystallizable and main-chain crystallizable polymers, the difference being that the former class of compounds contain crystallizable side-chain moieties, and the latter class are rendered crystallizable by their backbone structure. Depending on the embodiment, the polymer selected for incorporation into the adhesive assembly will comprise different monomers which provide the composition with the desired phase-transition temperature and tack. The adhesive composition may also be formulated so as to contain two or more different polymers as described herein.

Side-chain crystallizable polymers, sometimes called "comb-like" polymers, are well-known and available commercially. These polymers are reviewed in *J. Polymer Sci.: Macromol. Rev.* 8:117–253 (1974), the disclosure of which is hereby incorporated by reference. In general, these polymers contain monomer units X of the formula:

wherein M is a backbone atom, S is a spacer unit and C is a crystallizable group. These polymers have a heat of fusion ($\Delta H_f$) of at least about 20 Joules/g, preferably at least about 40 Joules/g. The polymers will contain about 50 to 100% monomer units represented by "X". If the polymer contains less than 100% X, it will in addition contain monomer units which may be represented by "Y" or "Z", or both, wherein Y is any polar or nonpolar monomer or mixture of polar or nonpolar monomers capable of polymerizing with X and/or Z, and wherein Z is a polar monomer or mixture of polar monomers. Polar groups —e.g., polyoxyalkylenes, acrylates including hydroxyethylacrylate, acrylamides including methacrylamide —will typically increase adhesion to most substrates. If the polar species "Z" is acrylic acid, it is preferred that it comprise about 1–10 wt. % of the polymer.

The backbone of the polymer (defined by "M") may be any organic structure (aliphatic or aromatic hydrocarbon, ester, ether, amide, etc.) or an inorganic structure (sulfide, phosphazine, silicone, etc.), and may include spacer linkages which can be any suitable organic or inorganic unit, for example ester, amide, hydrocarbon, phenyl, ether, or ionic salt (e.g., a carboxyl-alkyl ammonium or sulphonium or phosphonium ion pair or other known ionic salt pair).

The side-chain (defined by "S" and "C") may be aliphatic or aromatic or a combination of aliphatic and aromatic, but must be capable of entering into a crystalline state. Common examples are: linear aliphatic side-chains of at least 10 carbon atoms, e.g., $C_{14}$–$C_{22}$ acrylates or methacrylates, acrylamides or methacrylamides, vinyl ethers or esters, siloxanes or alpha olefins; fluorinated aliphatic side-chains of at least 6 carbons; and p-alkyl styrene side-chains wherein the alkyl is of 8 to 24 carbon atoms.

The length of the side-chain moiety is usually greater than 5 times the distance between side-chains in the case of acrylates, methacrylates, vinyl esters, acrylamides, methacrylamides, vinyl ethers and alpha olefins. In the extreme case of a fluoroacrylate alternate copolymer with butadiene, the side-chain can be as little as two times the length as the distance between the branches. In any case, the side-chain units should make up greater than 50% of the volume of the polymer, preferably greater than 65% of the volume.

Specific examples of side-chain crystallizable monomers are the acrylate, fluoroacrylate, methacrylate and vinyl ester polymers described in *J. Poly. Sci.* 10:3347 (1972); *J. Poly. Sci.* 10:1657 (1972); *J. Poly. Sci.* 9:3367 (1971); *J. Poly. Sci.* 9:3349 (1971); *J. Poly. Sci.* 9:1835 (1971); *J.A.C.S.* 76:6280 (1954); *J. Poly. Sci.* 7:3053 (1969); *Polymer J.* 17:991 (1985), corresponding acrylamides, substituted acrylamide and maleimide polymers (*J. Poly. Sci.: Poly. Physics Ed.* 18:2197 (1980); polyalphaolefin polymers such as those described in *J. Poly.*

Sci.: Macromol. Rev. 8:117-253 (1974) and *Macromolecules* 13:12 (1980), polyalkylvinylethers, polyalkylethylene oxides such as those described in *Macromolecules* 13:15 (1980), alkylphosphazene polymers, polyamino acids such as those described in *Poly. Sci. USSR* 21:241, *Macromolecules* 18:2141, polyisocyanates such as those described in *Macromolecules* 12:94 (1979), polyurethanes made by reacting amine- or alcohol-containing monomers with long-chain alkyl isocyanates, polyesters and polyethers, polysiloxanes and polysilanes such as those described in *Macromolecules* 19:611 (1986), and p-alkylstyrene polymers such as those described in *J.A.C.S.* 75:3326 (1953) and *J. Poly. Sci.* 60:19 (1962).

Of specific utility are polymers which are both relatively polar and capable of crystallization, but wherein the crystallizing portion is not affected by moisture. For example, incorporation of polyoxyethylene, polyoxypropylene, polyoxybutylene or copolyoxyalkylene units in the polymer will make the polymer more polar, improving adhesion to moist skin.

In a particularly preferred embodiment herein, in the above structure, —C is selected from the group consisting of —$(CH_2)_n$—$CH_3$ and —$(CF_2)_n$—$CF_2H$, where n is an integer in the range of 8 to 20 inclusive, —S— is selected from the group consisting of —O—, —$CH_2$—, —(CO)—, —O(CO)— and —NR— where R is hydrogen or lower alkyl (1-6C), and —M— is —$[(CH_2\text{-})_m$—CH]— where m is 0 to 2.

Typical "Y" units include linear or branched alkyl or aryl acrylates or methacrylates, alpha olefins, linear or branched alkyl vinyl ether or vinyl esters, maleic esters or itaconic acid esters, acrylamides, styrenes or substituted styrenes, acrylic acid, methacrylic acid and hydrophilic monomers as detailed in WO84/0387, cited supra.

In addition to the above-described monomer units "M-S-C", monomer structures given by

may in addition, or in the alternative, be present in the polymer. "D" is a hydrophilic polyether chain such as a polyoxyalkylene chain (e.g., polyoxyethylene) which, in contrast to "C", may or may not be crystallizable. "D" preferably has a molecular weight higher than about 100.

Preferred main-chain crystallizable polymers include water-insoluble polyalkylene oxides, lower alkyl polyesters and polytetrahydrofuran.

The crystallizable polymer, whether side-chain or main-chain crystallizable, may or may not be cross-linked. Cross-linking the adhesive composition will in general result in a material that exhibits decreased melt flow and greater cohesive strength than non-cross-linked materials. Because the adhesive composition may be used at temperatures above the melting point of the polymer, low melt flow is desirable so that the adhesive will not migrate, flow or transfer to the substrate surface (i.e., in contrast to conventional "hot-melt" adhesives). Adhesive compositions with sufficient cohesive strength to prevent cohesive failure is thus desirable. Low melt flow and suitable cohesive strength may be achieved by conducting polymerization under conditions that lead to high molecular weight, by addition of suitable co-monomers (e.g., high Tg monomers), by use of block copolymerization or other art-known methods, or by inducing cross-linking before, during or after preparation of the adhesive assembly.

A variety of methods are available to produce cross-linked side-chain crystallizable materials. A network copolymer can be prepared by polymerizing a side-chain crystallizable monomer and a multifunctional monomer either in one or two steps. A one-step process may be used to form an adhesive in place, while a two-step process is useful where an intermediate processing step is necessary. A variety of multifunctional monomers (di-, tri- or multifunctional acrylic or methacrylic esters, vinyl ethers, esters or amides, isocyanates, aldehydes, epoxies and the like) are known in the art. These multifunctional monomers can be used in a one- or two-step process depending on the desired result. Ionizing radiation, for example beta or gamma radiation, peroxides, silanes, or similar cure agents, can be used to cross-link a preformed side-chain crystallizable polymer with or without added comonomers. Ionic cross-links can be formed by, for example, reacting an acidic polymer site with a di- or trivalent metal salt or oxide to produce a complex which serves as a cross-link site. Likewise, organic salts or complexes can be prepared by methods known in the art.

If the material is cross-linked to too great an extent, crystallinity and/or tack may be decreased to the point that the desirable temperature-sensitive properties are lost. To optimize the aforementioned factors, it is preferred that cross-linking be in the range of 0.01 percent to 10 mole percent. The cross-linked polymers will normally have a heat of fusion of at least about 20 Joules/g, typically at least 30 Joules/g.

Effective cross-linking may also be obtained by physical methods. For example, a block copolymer of a crystallizable polymer and a second polymer which exhibits a glass transition or melting point higher than the crystallizable polymer may be prepared wherein the entire mass exhibits mechanical stability above the melting point of the crystallizable polymer but below the transition of the second polymer.

The adhesive compositions useful herein may include, in addition to one or more polymers as described above, conventional additives such as tackifiers (wood rosin, polyesters, etc.), antioxidants, fibrous or nonfibrous fillers, colorants, and the like. It is also possible to include additional adhesives, providing that the overall temperature-sensitivity profile is not significantly affected. It is preferred that the amount of crystallizable polymer in the adhesive composition be in the range of about 40 wt. % to about 100 wt. %.

Coating of the body members, or substrates, with the temperature-sensitive adhesive composition may be done in any number of ways, e.g., by spray deposition, painting, dipping, gravure printing, rolling, or the like. The adhesive composition may also be applied by transfer from a release sheet, i.e., in a manner similar to that involved in transfer printing. The composition may be applied neat, or in a suitable solvent or as an emulsion or latex. Alternatively, a mixture of the appropriate monomers and additives may be applied directly to a substrate and cured in place by heat, irradiation, or other suitable art-known processes.

In adhesive tapes and sheets, specifically, the backing onto which the temperature-sensitive adhesive composition is coated may comprise any number of backings which are well-known in the medical or surgical fields.

Thus, the backing may be a woven or nonwoven fabric, paper, or a synthetic film. Depending on the specific medical application, the backing may or may not be occlusive.

It will be appreciated by those skilled in the art that the temperature-sensitive adhesive compositions and adhesive assemblies described herein are useful in a variety of medical applications, i.e., in binding adhesive tape, bandaids, immobilization devices, transdermal drug delivery devices, surgical dressings, EKG electrodes, etc., to skin.

The foregoing description as well as the examples which follow are intended to illustrate and not limit the scope of the invention.

EXAMPLES

Experimental:

Melting temperatures and heats of fusion were determined using Differential Scanning Calorimetry (DSC) at a heating rate of 10° C./min. Heats of fusion ($\Delta H_f$) are expressed in J/g.

Crystallization temperatures were also determined by DSC, at a cooling rate of 10° C./min.

Peel strength: Peel strength was measured as follows. A solution (50% solids) of adhesive formulation was prepared in tetrahydrofuran, cast onto a flexible PVC film, and air-dried at 70° C. for 30 minutes. A 1"wide strip was covered with a 1"uncoated strip of the PVC film. The assembly was lightly pressed together at a temperature of 37° C. Average peel strength was measured at 10"/min using an Instron materials testing instrument equipped with a variable temperature chamber.

Tack measurement: Tack was measured using a Surface Texture Analyzer (a Voland-Stevens-LFRA Texture Analyzer). The probe was allowed to contact the adhesive for 10 seconds and was then withdrawn at 0.2 mm/sec. Tack values reported herein are the average maximum reading.

Measurement of tack temperature: A 1"×"1" test sample was bonded face up to a metal plate with double sided adhesive tape and the metal plate was placed in a temperature controlled oven and allowed to equilibrate at the selected temperature for 10 minutes. Tack was tested by lightly pressing a 1 cm diameter plastic rod onto the surface of the adhesive for 1 second and then removing. After testing at the lowest temperature, the oven temperature was increased by 2° C. and test repeated. The tack temperature is defined as the minimum temperature at which a noticeable tack was first observed.

EXAMPLE 1

A polymer was prepared by combining 10 g of hexadecyl acrylate, 2 g of ethyl acrylate, 15 ml of deoxygenated toluene, and 0.06 g of AIBN, and heating at 60° C. under a nitrogen atmosphere for 12 hours. The resulting mass was extracted with ethanol and dried in vacuo to yield a rubbery mass. Thermal analysis showed that this material had a melting point of 34° C., a freezing point of 26° C., and a heat of fusion of 64 J/g. A sample of this material was heated to 70° C. and pressed into a 0.001"-thick film. A sample of the film was placed onto the adhesive side of a commercial plastic-backed PSA tape and stored at 25° C. The resulting tape was nontacky to the touch and exhibited no tack or adhesion to paper at room temperature. When the tape was placed on the wrist of a human subject, however, it became tacky almost instantly and exhibited good adhesion. When removed from the skin and kept at room temperature, the tape quickly lost its tack and adhesive properties.

EXAMPLE 2

Five percent acrylic acid, 5% ethylacrylate-hexadecylacrylate copolymer (1 g) was mixed with 1 ml of toluene and 0.04 g XAMA2 (Virginia Chemicals, Portsmouth, Va.) as cross-linking agent. The material was allowed to stand two days at 80° C. at which point it was more viscous. More toluene was added to make the solution spreadable. The mixture was then spread onto clear PVC film, dried at 80° C. for 1 hour, and allowed to cool. The composition displayed excellent adhesion to skin at body temperature and was easily removed with a cool, damp paper towel. This adhesive exhibited no tack at room temperature.

EXAMPLE 3

Sixteen grams of hexadecylacrylate, 3 grams of isodecylacrylate (Sartomer), 1 gram of acrylic acid, 0.100 gram of AIBN was combined with 30 ml of toluene, purged with nitrogen and reacted for 11 hours at 70° C. The resulting solution was precipitated into methanol and dried. Test samples were prepared by solution coating a 50% solids solution of the polymer in tetrahydrofuran onto a PVC backing and drying at 50° C. The dry thickness of the resulting adhesive was approximately 0.0025 cm. Crosslinked samples were prepared by addition of XAMA 2 to adhesive solution prior to coating and drying.

Tack and adhesive strength were measured at 20° C. and 39° C. as shown in Table I.

TABLE I

| Cure (% w/w) | TACK ($g/cm^2$) | | PEEL STRENGTH (g/cm) | |
|---|---|---|---|---|
| | (20° C.) | (39° C.) | (20° C.) | (39° C.) |
| 0 | 0 | >100 | <4.5 | 7 |
| 0.75 | 0 | 12 | <4.5 | — |
| 0.35 | 0 | 15 | <4.5 | 21 |

EXAMPLE 4

Nineteen grams of pentadecylacrylate and 1 gram of acrylic acid were combined with 20 ml of heptane, 10 ml of ethyacetate and 0.070 grams of AIBN. Resulting solution was degassed and mixed at 70° C. for 17 hours. Polymer was isolated and dried in vacuo.

One gram of polymer and 0.003 grams of XAMA 2 was dissolved into 2 ml of 1:1 heptane:ethylacetate and coated onto a 0.005 cm thick polyurethane backing (2103 AE, Dow Chemical, Midland, Mich.) and dried at 80° C. for 15 minutes. The resulting tape was nontacky at room temperature but quickly adhered upon application to skin. During a 36 hour test on a human subject no disbondment of adhesive or film from skin was observed.

EXAMPLE 5

Two grams of a hexadecylacrylate, thylacrylate, acrylic acid co-polymer (76.5:20:2.5) was combined with 4 ml of 1:1 ethylacrylatee:heptane solution and 0.0043 grams of XAMA 2. The resulting solution was coated onto urethane film and dried at 110° C. for 15 minutes. The obtained film was not tacky at 25° C. but bonded readily to a human subject. Samples showed no loss in adhesion when subjected to washing. During a 36-hour test no delamination of adhesive was observed.

EXAMPLE 6

The polymer of Example 3 alone and with 0.3% XAMA 2 was coated onto urethane backing and dried at 110° C. for 15 minutes. Both samples were nontacky at room temperature and quickly became tacky when contacted to human skin. Three 1"×1" test samples were applied to a test subject for seven hours. At that time it was observed that the non-crosslinked samples had lifted off from the skin around the edges and left a tacky residue on the skin when removed. The cross-linked sample in contrast stayed well bonded and left no tacky residue on the skin upon removal.

EXAMPLE 7

A co-polymer of hexadecylacrylate, methylacrylate and acrylic acid (weight ratio 85:10:5) was prepared as in Example 3 above. A 1 gram sample was combined with 0.0024 grams of XAMA 2, 1 ml of heptane, 1 ml of ethyl acetate and coated onto a urethane backing and cured as in Example 6 above. Six 2.54 cm×2.54 cm test samples were applied to a human test subject for 26 hours. Three of the samples were removed at ambient temperature and three of the samples were chilled for 20 seconds with a cold Pepsi can prior to removal. All of the samples removed at ambient temperature resulted in visible amounts of skin being removed from the test subject. Two of the cooled samples showed no visible skin removal, while the third showed a very small amount of skin removal.

EXAMPLE 8

The cross-linked adhesive coated urethane of Example 5 above was applied to a sample of Tuftane 410 polymer film (Lord Corporation, Erie, Pa.) and warmed to 35° C. Material bonded well at this temperature but exhibited no adhesion when cooled to 20° C.

EXAMPLE 9

One gram of polyoctadecylmethacrylate acrylic acid co-polymer (97.5:2.5) was combined with 1 ml of ethylacetate, and 0.0028 g of XAMA 2 and coated onto a urethane backing as in Example 6 above. Four 1"×1" samples were applied to a human test subject. After 24 hours two of the samples were removed at room temperature and two were first cooled with a cold Pepsi can and then removed. The two samples removed at ambient temperature showed visible skin removal while the samples which were first cooled showed no visible skin removal.

EXAMPLE 10

A polymer was prepared by polymerizing 4.25 g of hexdecyl acrylate, 4.24 g of tetradecyl acrylate 1.02 g of polyethyleneglycol monomethyl ether (DP=8) methacrylate and 0.50 g of acrylic acid in 20 ml of toluene containing 0.033 g of AIBN at 60° C. for 14 hours. A sample of the resultant polymer was combined with 0.25% XAMA 2 and coated onto a urethane backing as in Example 6 above.

EXAMPLE 11

Thirty-one grams of poly tetrahydrofuran of M.W. 2900, (Scientific Polymer Products, Ontario, N.Y.), 1.85 grams of hexamethylene diisocyanate, 1 drop of dibutyltin dilaurate and 200 ml of dry toluene were combined and mixed for 24 hours and then 5 ml of ethanol was added with stirring. The resultant mixture was coated onto a glass slide, dried at 100° C. for 1 hour and then allowed to cool overnight. The resulting film was nontacky at 10° C. but tacky at skin temperature yet showed no tendency to flow.

EXAMPLE 12

One gram of polytetrahydrofuran (M.W. 2900) and 3.0 grams of the polymer solution of Example 11 were combined and coated onto a glass microscope slide, dried at 100° C. for 12 hours and allowed to cool.

EXAMPLE 13

To 20 ml of toluene were added 8.5 grams of hexadecylacrylate, 1.0 grams of polyethyleneglycol monomethyl ether (DP=8) methacrylate, 0.5 grams of acrylic acid and 0.0667 grams of AIBN. The solution was purged with nitrogen and heated at 60° C. for 14 hours. The product was precipitated into ethanol, filtered and dried under vacuum.

Test samples were prepared by solution casting. The solution contained 2 grams of the above polymer and enough ethyl acetate to bring the total weight up to 6 grams. To portions of this solution was added 0, 1, 2 and 3% of XAMA-2. Each solution was cast on polyvinyl chloride film using a 8.7 cm wide blade set at 3 mil. The films were air dried and then heated for 1 hour at 58° C. The width of the respective films were 8.1, 7.6, 7.3, 6.8 cm., indicating that crosslinking had occurred to various degrees.

Each of the samples became tacky above a temperature of 36° C. It was apparent that the order of tackiness decreased as the amount of XAMA-2 was increased.

EXAMPLE 14

A polymer solution was prepared as in Example 13 with hexadecyl acrylate, ethyl acrylate and acrylic acid in an 80:15:5 ratio. Testing was carried out as described in Example 13.

The tack temperature measured as above for the compositions of Examples 3, 4, 5, 7, 10, 13 and 14 are set forth in Table II:

TABLE II

| Composition | % XAMA 2 (w/w) | Tack temperature |
| --- | --- | --- |
| Example 3 | 0 | 31 |
| Example 3 | 0.32 | 29 |
| Example 4 | 0.3 | 31 |
| Example 5 | 0.22 | 29 |
| Example 7 | 0 | 33 |
| Example 7 | 0.30 | 33 |
| Example 10 | 0.25 | 27 |
| Example 13 | — | 33 |
| Example 14 | 0.25 | 29 |

I claim:

1. A temperature-sensitive adhesive assembly for application to the skin, comprising a body member having a surface coated with a polymeric adhesive composition which is substantially nontacky at or below about 25° C. and which becomes tacky upon contact with the skin, wherein the adhesive composition comprises a side-chain crystallizable polymer having a heat of fusion that is greater than about 20 Joules/g, and a melting point or first-order transition temperature in the range of about 20° C. to 35° C., and wherein the side-chain crystallizable polymer contains at least about 50% monomer units of the structure

wherein M is a backbone atom and —S—C is a side-chain in which S is a spacer unit and C is a crystallizable group, and wherein the length of the side-chain is greater than five times the distance between adjacent side-chains in the polymer, and wherein the body member is a flexible backing, a cast, a splint, a transdermal drug delivery device, a bandaid, a medicated bandaid, a surgical dressing, or an EKG electrode.

2. The adhesive assembly of claim 1, wherein the side-chain crystallizable polymer has a melting point or first-order transition temperature in the range of about 25° C. to 30° C.

3. The adhesive assembly of claim 1, wherein the side-chain crystallizable polymer comprises at least 50 wt. % monomer units selected from the group consisting of: linear aliphatic $C_{14}$–$C_{22}$ acrylates and methacrylates; linear aliphatic $C_{14}$–$C_{22}$ acrylamides and methacrylamides; vinyl ethers and esters; siloxanes; and alpha olefins.

4. The adhesive assembly of claim 1 comprising temperature-sensitive adhesive tape, wherein the body member is a flexible backing.

5. The adhesive assembly of claim 1 comprising a temperature-sensitive adhesive sheet.

6. A temperature-sensitive adhesive assembly for application to the skin which is readily removable therefrom upon cooling, comprising a body member having a surface coated with a polymeric adhesive composition comprising a side-chain crystallizable polymer which has a heat of fusion that is greater than about 20 Joules/g, and a freezing point in the range of about 10° C. to about 28° C., and wherein the side-chain crystallizable polymer contains at least about 50% units of the structure

wherein M is a backbone atom, S is a spacer unit, and C is a crystallizable group and wherein the body member is a flexible backing, a the length of the side chains is greater than 5 times the distance between adjacent side chains in the polymer cast, a splint, a transdermal drug delivery device, a bandaid, a medicated bandaid, a surgical dressing, or an EKG electrode.

7. The adhesive assembly of claim 1, wherein the freezing point is in the range of about 15° C. to 25° C.

8. The adhesive assembly of claim 6, wherein the side-chain crystallizable polymer comprises at least 50 wt. % monomer units selected from the group consisting of: linear aliphatic $C_{14}$–$C_{22}$ acrylates and methacrylates; linear aliphatic $C_{14}$–$C_{22}$ acrylamides and methacrylamides; vinyl ethers and esters; siloxanes; and alpha olefins.

9. The adhesive assembly of claim 6 comprising temperature-sensitive adhesive tape, wherein the body member is a flexible backing.

10. The adhesive assembly of claim 6 comprising a temperature-sensitive adhesive sheet.

11. A temperature-sensitive adhesive assembly for application to the skin which is readily removable therefrom upon cooling, comprising a body member having a surface coated with a polymeric adhesive composition which is substantially nontacky at or below about 25° C. and which becomes tacky upon contact with the skin, comprising a side-chain crystallizable polymer having a heat of fusion of greater than about 20 Joules/g and which has a melting point or first-order transition temperature in the range of about 20° C. to 35° C. and a freezing point in the range of about 10° C. to 28° C., and wherein the side-chain crystallizable polymer contains at least 50% monomer units of the structure

wherein M is a backbone atom, S is a spacer unit, and C is a crystallizable group, and wherein the body member is a flexible backing, a the length of the side chain is greater than 5 times the distance between adjacent side chains in the polymer cast, a splint, a tranderdmal drug delivery device, a bandaid, a medicated bandaid, a surgical dressing, or an EKG electrode.

12. The adhesive assembly of claim 1, wherein the melting point or first-order transition temperature is in the range of about 25° C. to 30° C. and the freezing point is in the range of about 15° C. to 25° C.

13. The adhesive assembly of claim 11, wherein the side-chain crystallizable polymer comprises at least 50 wt. % monomer units selected from the group consisting of: linear aliphatic $C_{14}$–$C_{22}$ acrylates and methacrylates; linear aliphatic $C_{14}$–$C_{22}$ acrylamides and methacrylamides; vinyl ethers and esters; siloxanes; and alpha olefins.

14. The adhesive assembly of claim 11 comprising temperature-sensitive adhesive tape, wherein the body member is a flexible backing.

15. The adhesive assembly of claim 11 comprising a temperature-sensitive adhesive sheet.

16. A temperature-sensitive adhesive assembly for application to the skin which is readily removable therefrom upon cooling, comprising a body member having a surface coated with a polymeric adhesive composition which is substantially nontacky at or below about 25° C. and which becomes tacky upon contact with the skin, comprising a side-chain crystallizable polymer having a heat of fusion of greater than about 20 Joules/g and a melting point or first-order transition temperature in the range of about 20° C. to 35° C. and a freezing point in the range of about 10° C. to 28° C., wherein the side-chain crystallizable polymer comprises at least 50 wt. % monomer units selected from the group consisting of: linear aliphatic $C_{14}$–$C_{22}$ acrylates and methacrylates; linear aliphatic $C_{14}$–$C_{22}$ acrylamides and methacrylamides; vinyl ethers and esters; siloxanes; and alpha olefins, and wherein the body member is a flexible backing, a cast, a splint, a transdermal drug delivery device, a bandaid, a medicated bandaid, a surgical dressing, or an EKG electrode.

17. The adhesive assembly of claim 16, wherein the side-chain crystallizable polymer comprises at least 50 wt. % monomer units selected from the group consisting of linear aliphatic $C_{14}$–$C_{22}$ acrylates and methacrylates.

18. A temperature-sensitive adhesive assembly for application to the skin, comprising a body member having a surface coated with a polymeric adhesive composition which is substantially nontacky at or below about 25° C. and which becomes tacky upon contact with the skin, wherein the adhesive composition comprises a main-chain crystallizable polymer having a heat of fusion that is greater than about 20 Joules/g, and a melting point or first-order transition temperature in the range of about 20° C. to 35° C., and wherein the main-chain crystallizable polymer is selected from the group consisting of a water-insoluble polyethylene oxide, a lower alkyl polyester, and polytetrahydrofuran, and wherein the body member is a flexible backing, a cast, a splint, a transdermal drug delivery device, a bandaid, a medicated bandaid, a surgical dressing, or an EKG electrode.

19. A temperature-sensitive adhesive assembly for application to the skin which is readily removable therefrom upon cooling, comprising a body member having a surface coated with a polymeric adhesive composition comprising a main-chain crystallizable polymer which has a heat of fusion that is greater than about 20 Joules/g, and a freezing point in the range of about 10° C. to about 28° C., and wherein the main-chain crystallizable polymer is selected from the group consisting of a water-insoluble polyethylene oxide, a lower alkyl polyester, and polytetrahydrofuran, and wherein the body member is a flexible backing, a cast, a splint, a transdermal drug delivery device, a bandaid, a medicated bandaid, a surgical dressing, or an EKG electrode.

20. A temperature-sensitive adhesive assembly for application to the skin which is readily removable therefrom upon cooling, comprising a body member having a surface coated with a polymeric adhesive composition which is substantially nontacky at or below about 25° C. and which becomes tacky upon contact with the skin, comprising a main-chain crystallizable polymer having a heat of fusion of greater than about 20 Joules/g and which has a melting point or first-order transition temperature in the range of about 20° C. to 35° C. and a freezing point in the range of about 10° C. to 28° C., and wherein the main-chain crystallizable polymer is selected from the group consisting of a water-insoluble polyethylene oxide, a lower alkyl polyester, and polytetrahydrofuran, and wherein the body member is a flexible backing, a cast, a splint, a transdermal drug delivery device, a bandaid, a medicated bandaid, a surgical dressing, or an electrode.

* * * * *